US011642186B2

(12) United States Patent
Ago et al.

(10) Patent No.: US 11,642,186 B2
(45) Date of Patent: May 9, 2023

(54) ADAPTOR AND METHOD OF ATTACHING SURGICAL INSTRUMENT TO ROBOT ARM THROUGH ADAPTOR

(71) Applicant: MEDICAROID CORPORATION, Kobe (JP)

(72) Inventors: Kenji Ago, Kobe (JP); Kaoru Takahashi, Kobe (JP); Yu Usuki, Kobe (JP); Shota Betsugi, Kobe (JP); Tomoaki Noda, Kobe (JP); Yoshiaki Tanaka, Kobe (JP); Tetsuya Nakanishi, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 907 days.

(21) Appl. No.: 16/542,300

(22) Filed: Aug. 16, 2019

(65) Prior Publication Data

US 2020/0069385 A1    Mar. 5, 2020

(30) Foreign Application Priority Data

Aug. 28, 2018  (JP) .............................. JP2018-159332
Mar. 28, 2019  (JP) .............................. JP2019-063447

(51) Int. Cl.
*A61B 34/37*    (2016.01)
*A61B 34/00*    (2016.01)
(Continued)

(52) U.S. Cl.
CPC .............. *A61B 34/37* (2016.02); *A61B 34/70* (2016.02); *A61B 46/10* (2016.02); *A61B 90/50* (2016.02);
(Continued)

(58) Field of Classification Search
CPC combination set(s) only.
See application file for complete search history.

(56) References Cited

U.S. PATENT DOCUMENTS 7,699,855 B2    4/2010  Anderson et al.
8,998,930 B2    4/2015  Orban, III
(Continued)

FOREIGN PATENT DOCUMENTS

CN    102630154 A    8/2012
CN    106102641 A    11/2016
(Continued)

*Primary Examiner* — Scott Luan
(74) *Attorney, Agent, or Firm* — Metrolex IP Law Group, PLLC

(57) ABSTRACT

An adaptor for detachably connecting a surgical instrument to a robot arm of a robotic surgical system according to an embodiment may include: a base body including a first surface to be attached to the robot arm and a second surface to which an attachment surface of the surgical instrument is mounted; and drive transmission members rotatably provided on the base body. The second surface of the base body includes first and second guide rails respectively corresponding to first and second guide grooves provided on the attachment surface of the surgical instrument. The first and second guide rails of the second surface are configured to be inserted respectively into the first and second guide grooves of the attachment surface, and guide the surgical instrument to be slid to a position where the drive transmission members respectively correspond to rotation members provided on the attachment surface of the surgical instrument.

19 Claims, 13 Drawing Sheets

(51) Int. Cl.
    *A61B 90/50*         (2016.01)
    *A61B 46/10*         (2016.01)
    *A61B 17/00*         (2006.01)
    *A61B 34/30*         (2016.01)

(52) U.S. Cl.
    CPC ........... *A61B 2017/00477* (2013.01); *A61B 2017/00973* (2013.01); *A61B 2034/301* (2016.02); *A61B 2034/305* (2016.02)

(56) References Cited

U.S. PATENT DOCUMENTS

| | | |
|---|---|---|
| 2006/0235436 A1 | 10/2006 | Anderson et al. |
| 2010/0228249 A1* | 9/2010 | Mohr .................... A61B 34/37 715/764 |
| 2017/0172549 A1 | 6/2017 | Smaby et al. |
| 2018/0168752 A1 | 6/2018 | Scheib et al. |

FOREIGN PATENT DOCUMENTS

| | | |
|---|---|---|
| JP | 2007-167644 A | 7/2007 |
| WO | 2011/037394 A2 | 3/2011 |
| WO | 2011/037394 A3 | 3/2011 |
| WO | 2015/142958 A1 | 9/2015 |
| WO | 2018/119136 A1 | 6/2018 |

* cited by examiner

ADAPTOR AND METHOD OF ATTACHING SURGICAL INSTRUMENT TO ROBOT ARM THROUGH ADAPTOR

CROSS REFERENCE TO RELATED APPLICATIONS

This application claims priority to Japanese Patent Application No. 2018-159332 filed on Aug. 28, 2018 and Japanese Patent Application No. 2019-063447 filed on Mar. 28, 2019, the entire contents of which are incorporated herein by reference.

BACKGROUND

The disclosure relates to an adaptor, and particularly relates to an adaptor that detachably connects a surgical instrument to a robot arm of a robotic surgical system, and to a method of attaching the surgical instrument to the robot arm through the adaptor.

In a related art, there has been known an adaptor that detachably connects a surgical instrument to a robot arm of a robotic surgical system (e.g., see U.S. Pat. No. 8,998,930).

U.S. Pat. No. 8,998,930 discloses an adaptor including a retaining member that is engaged with a tab provided in a side section of a surgical instrument and an input section that transmits driving force of a robot arm to the surgical instrument. In the adaptor disclosed in U.S. Pat. No. 8,998,930, the retaining member is formed to cover the tab from the outside.

SUMMARY

However, since the retaining member of the adaptor disclosed in U.S. Pat. No. 8,998,930 is formed to cover the tab provided in the side section of the surgical instrument from the outside, the adaptor needs to be formed wider than a section of the surgical instrument to be attached to the adaptor. This leads to a problem of difficulty in downsizing the adaptor.

An object of an embodiment of the disclosure is to downsize an adaptor that detachably connects a surgical instrument to a robot arm of a robotic surgical system.

A first aspect of an embodiment may be an adaptor for detachably connecting a surgical instrument to a robot arm of a robotic surgical system. The adaptor may include a base body and drive transmission members. The base body includes a first surface to be attached to the robot arm and a second surface to which an attachment surface of the surgical instrument is mounted. The drive transmission members are rotatably provided on the base body. The second surface of the base body includes a first guide rail and a second guide rail corresponding to a first guide groove and a second guide groove provided on the attachment surface of the surgical instrument. The first and second guide rails of the second surface are configured to be inserted into the first and second guide grooves of the attachment surface respectively, to guide the surgical instrument to be slid to a position where the drive transmission members correspond to rotation members provided on the attachment surface respectively.

A second aspect of an embodiment may be an adaptor for detachably connecting a surgical instrument to a robot arm of a robotic surgical system. The adaptor may include a base body and a drive transmission member. The base body includes a first surface to be attached to the robot arm and a second surface to which an attachment surface of the surgical instrument is mounted. The drive transmission member is rotatably provided on the base body. The second surface of the base body includes a first guide rail and a second guide rail corresponding to a first guide groove and a second guide groove provided on the attachment surface of the surgical instrument. The first and second guide rails of the second surface are configured to be inserted into the first and second guide grooves of the attachment surface respectively, to guide the surgical instrument to be slid to a position where the drive transmission member corresponds to a rotation member provided on the attachment surface. The adaptor further includes a precedence guide section that is formed to protrude from the base body along a direction parallel to a direction in which the first and second guide rails extend and that guides the surgical instrument before the first and second guide rails guide the surgical instrument.

A third aspect of an embodiment may be a method of attaching a surgical instrument to a robot arm of a robotic surgical system through an adaptor.

The method may include: attaching a first surface of a base body of the adaptor to the robot arm; bringing a protrusion protruding from an attachment surface of the surgical instrument into contact with a precedence guide section formed to protrude from the base body; moving the surgical instrument in a slide insertion direction while the protrusion is slidably guided by the precedence guide section; inserting a first guide rail and a second guide rail provided on a second surface of the base body into a first guide groove and a second guide groove provided on the attachment surface respectively, and moving the surgical instrument with respect to the adaptor to a position where drive transmission members rotatably provided on the base body correspond to rotation members provided on the attachment surface respectively while the first and second guide rails are slidably guided by the first and second guide grooves; and engaging the protrusion of the surgical instrument with an attachment engagement section of the adaptor.

DETAILED DESCRIPTION

Figure 1:
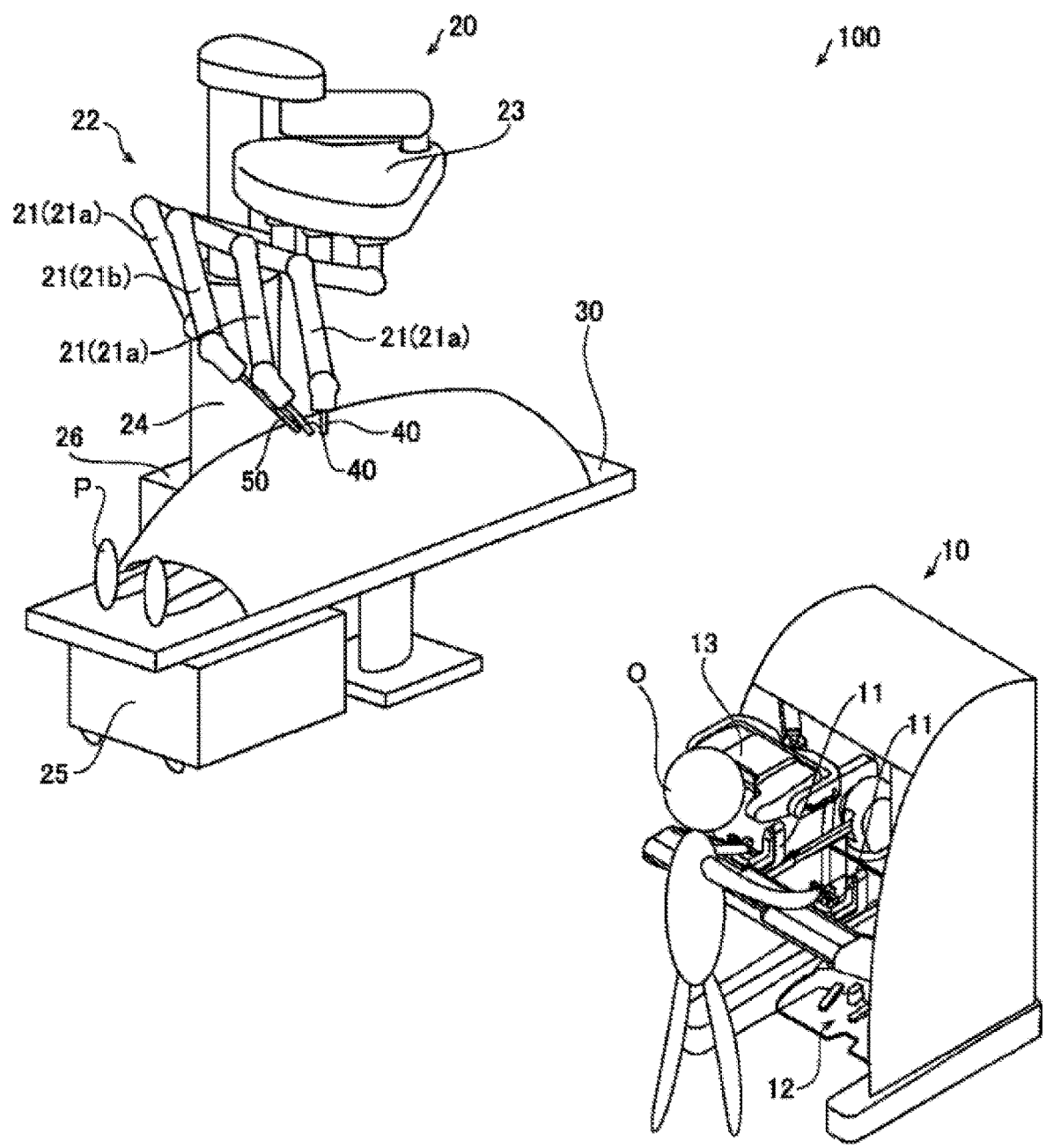
FIG. 1 is a diagram illustrating an overview of a robotic surgical system according to a first embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

First Embodiment (Configuration of Robotic Surgical System)

The configuration of a robotic surgical system 100 according to a first embodiment is described with reference to FIGS. 1 and 2.

As illustrated in FIG. 1, the robotic surgical system 100 includes a remote control apparatus 10 and a patient-side apparatus 20. The remote control apparatus 10 is provided to remotely control medical equipment provided for the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates medical equipment, including surgical instruments 40 and an endoscope 50, attached to robot arms 21. This allows minimally invasive surgery.

The patient-side apparatus 20 constitutes an interface to perform a surgery on a patient P. The patient-side apparatus 20 is positioned beside an operation table 30 on which the patient P is laid. The patient-side apparatus 20 includes robot arms 21. One of the robot arms 21 (21b) holds the endoscope 50 while the other robot arms 21 (21a) hold the surgical instruments 40. The robot arms 21 are commonly supported by a platform 23. Each of the robot arms 21 includes joints. Each joint includes a driver provided with a servo-motor and a position detector such as an encoder. The robot arms 21 are configured so that the medical equipment attached to each robot arm 21 is controlled by a driving signal given through the controller 26 and performs a desired movement.

The platform 23 is supported by a positioner 22 placed on the floor of an operation room. The positioner 22 includes a column 24 and a base 25. The column 24 includes an elevating shaft adjustable in the vertical direction. The base 25 includes wheels and is movable on the floor surface.

The surgical instruments 40 as the medical equipment are detachably attached to the distal ends of the robot arms 21a. Each surgical instrument 40 includes: a housing 43 (see FIG. 4), which is attached to the robot arm 21a; an elongated shaft 42 (see FIG. 4); and an end effector 41 (see FIG. 4), which is provided at the tip of the shaft 42. The end effector 41 is grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effectors 41 of the surgical instruments 40 are then located near the surgery site.

To the distal end of the robot arm 21b, the endoscope 50 as the medical equipment is detachably attached. The endoscope 50 captures an image within the body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate medical equipment attached to the robot arms 21. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed, for example.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object and include an action to supply current to a bipolar or monopolar instrument to burn off the surgery site.

The action modes to be executed by the endoscope 50 include the position and posture of the tip of the endoscope 50 and setting of the zoom magnification, for example.

Figure 2:
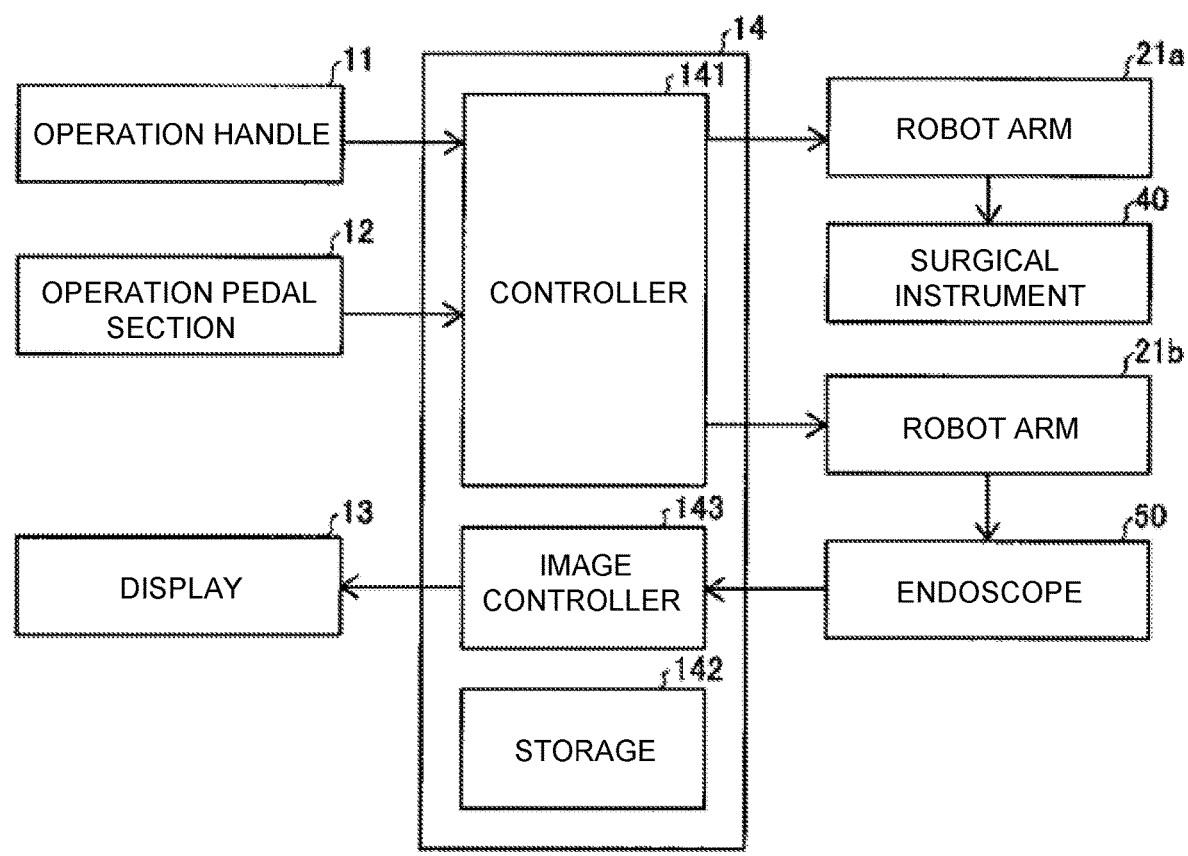
FIG. 2 is a block diagram illustrating a control-related configuration of the robotic surgical system according to a first embodiment.

As illustrated in FIGS. 1 and 2, the remote control apparatus 10 includes operation handles 11, an operation pedal section 12, a display section 13, and a control apparatus 14.

The operation handles 11 are provided in order to remotely operate medical equipment attached to the robot arms 21. Specifically, the operation handles 11 accept operations by the operator O for operating medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating section on the master side in the master-slave system, and the robot arms 21a and 21b holding medical equipment constitute an operating section on the slave side. When the operator O operates the operation handles 11, the movement of one of the robot arms 21a or 21b is controlled so that the tip (the end effector 41 of the surgical instrument 40) of the robot arm 21a or the tip (the endoscope 50) of the robot arm 21b moves following the movement of the operation handles 11.

The patient-side apparatus 20 controls the movement of the robot arms 21a in accordance with the set motion scaling ratio. When the motion scaling ratio is set to ½, for example, the end effectors 41 of the surgical instruments 40 move ½ of the movement distance of the operation handles 11. This allows precise fine surgery.

The operation pedal section 12 includes pedals to execute medical equipment-related functions. The pedals include a coagulation pedal, a cutting pedal, a camera pedal, and a clutch pedal. The pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate a surgery site. The cutting pedal enables the surgical instrument 40 to cut a surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. The position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21 to stop movement of the surgical instruments 40. Specifically, when the clutch pedal is being pressed, the robot arms 21 of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21. The operator O restarts the operation for the operation handles 11 around the center thereof.

The display section 13 is configured to display images captured by the endoscope 50. The display section 13 includes a scope type display section or a non-scope type display section. The scope type display section is a display section that the operator O looks into. The non-scope type display section is a display section like an open-type display section that includes a flat screen and the operator O is able to see without looking into, such as normal displays for personal computers.

When the scope type display section is attached, the scope type display section displays 3D images captured by the endoscope 50 attached to the robot arm 21b of the patient-side apparatus 20. When the non-scope type display section is attached, the non-scope type display section also displays 3D images captured by the endoscope 50 provided for the patient-side apparatus 20. The non-scope type display section may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be formed of a single controller performing centralized control or may be composed of controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display section 13. The image controller 143 performs processing and alternations for the images when needed.

(Configurations of Adaptor and Surgical Instrument)

With reference to FIGS. 3 to 11, the configurations of an adaptor 60 and the surgical instrument 40 according to a first embodiment are described.

Figure 3:
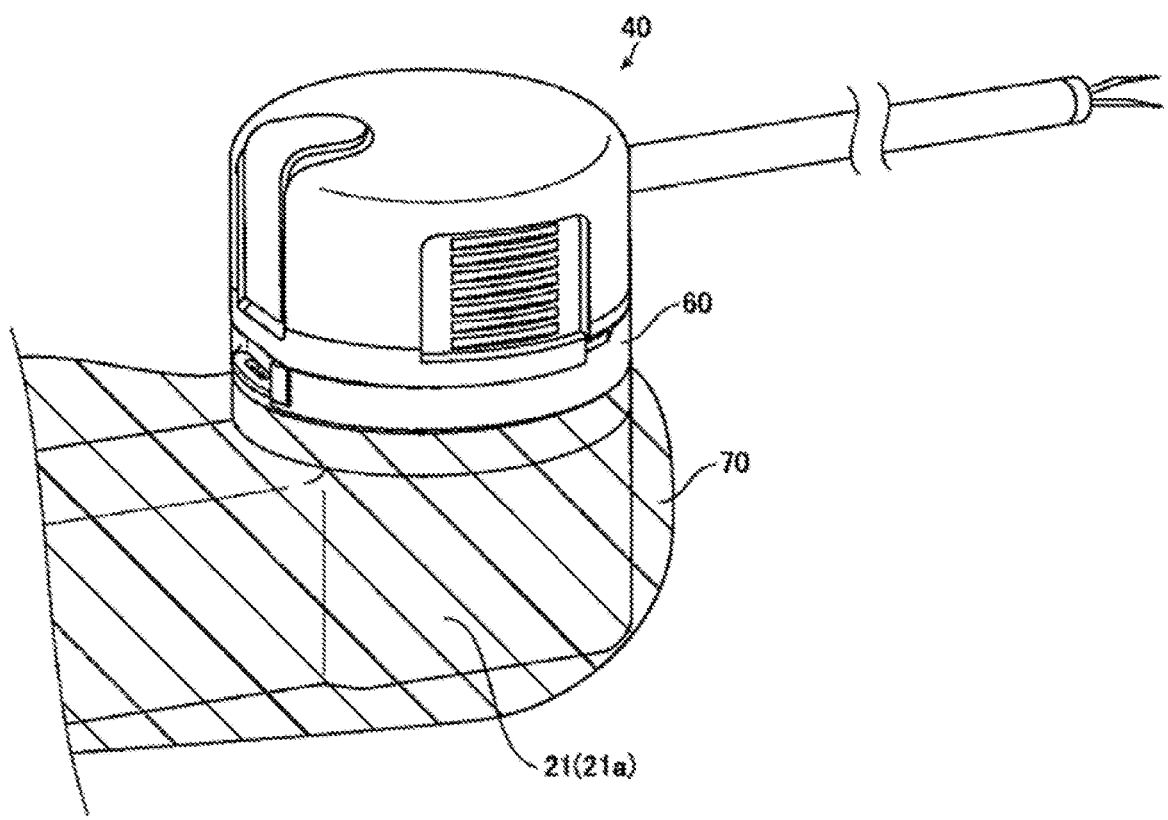
FIG. 3 is a diagram illustrating a perspective view of a state of a first embodiment where a surgical instrument is attached to a robot arm through an adaptor.

As illustrated in FIG. 3, the robot arm 21 is used in a clean area and is covered with a drape 70. In operation rooms, clean technique is used in order to prevent surgical incision sites and medical equipment from being contaminated by pathogen, foreign matters, or the like. The clean technique defines a clean area and a contaminated area, which is other than the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drapes 70.

The drape 70 is arranged between the robot arm 21 and the surgical instrument 40. Specifically, the drape 70 is arranged between the adaptor 60 and the robot arm 21. The adaptor 60 is attached to the robot arm 21 while putting the drape 70 between the adaptor 60 and the robot arm 21. Specifically, the adaptor 60 is a drape adaptor that puts the drape 70 between the adaptor 60 and the robot arm 21a. The surgical instrument is attached to the adaptor 60. The robot arm 21 transmits driving force to the surgical instrument 40 through the adaptor 60 to drive the end effector 41 of the surgical instrument 40.

Figure 4:
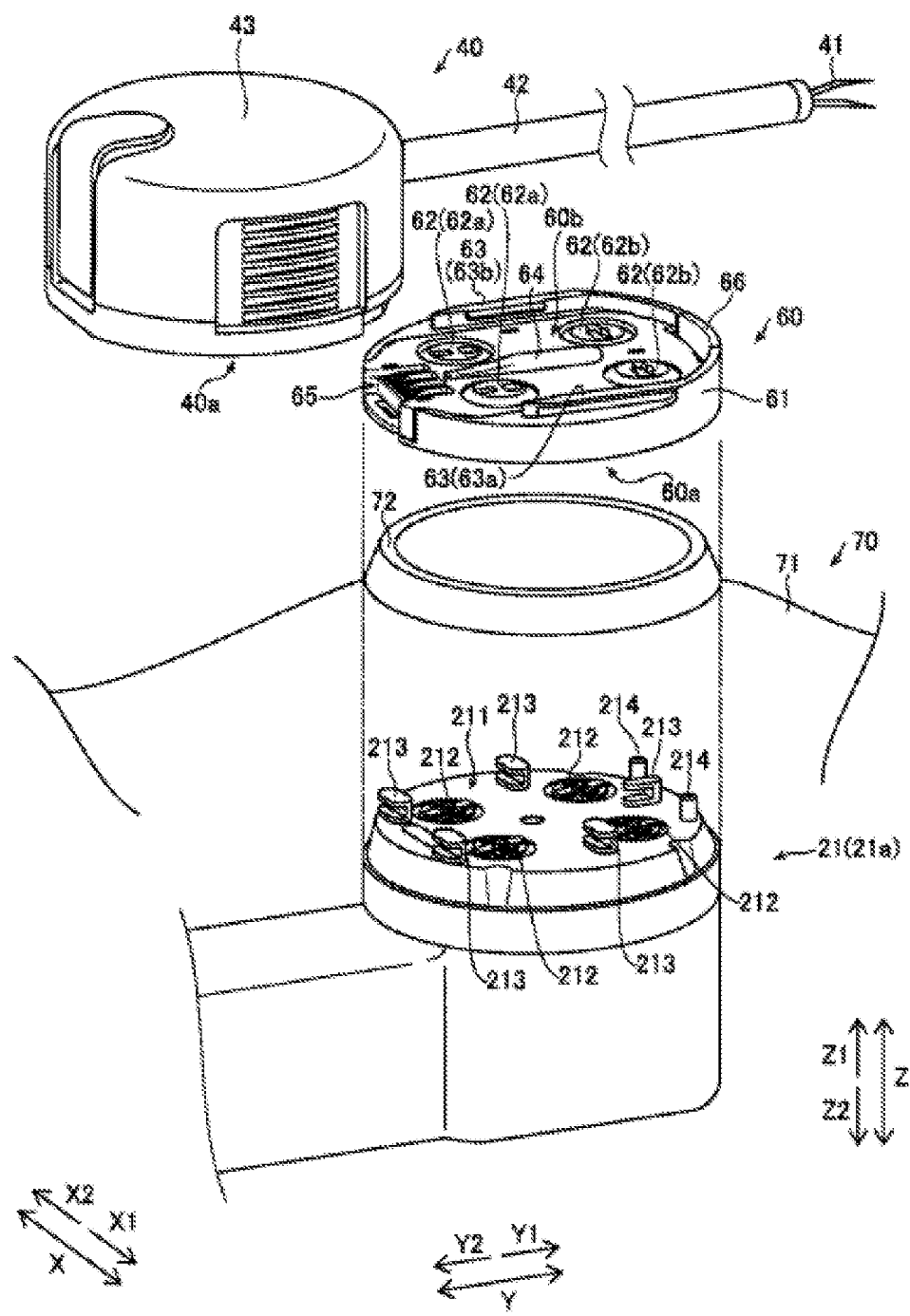
FIG. 4 is a diagram illustrating a perspective view of a state of a first embodiment where the surgical instrument and the adaptor are detached from the robot arm.
Figure 5:
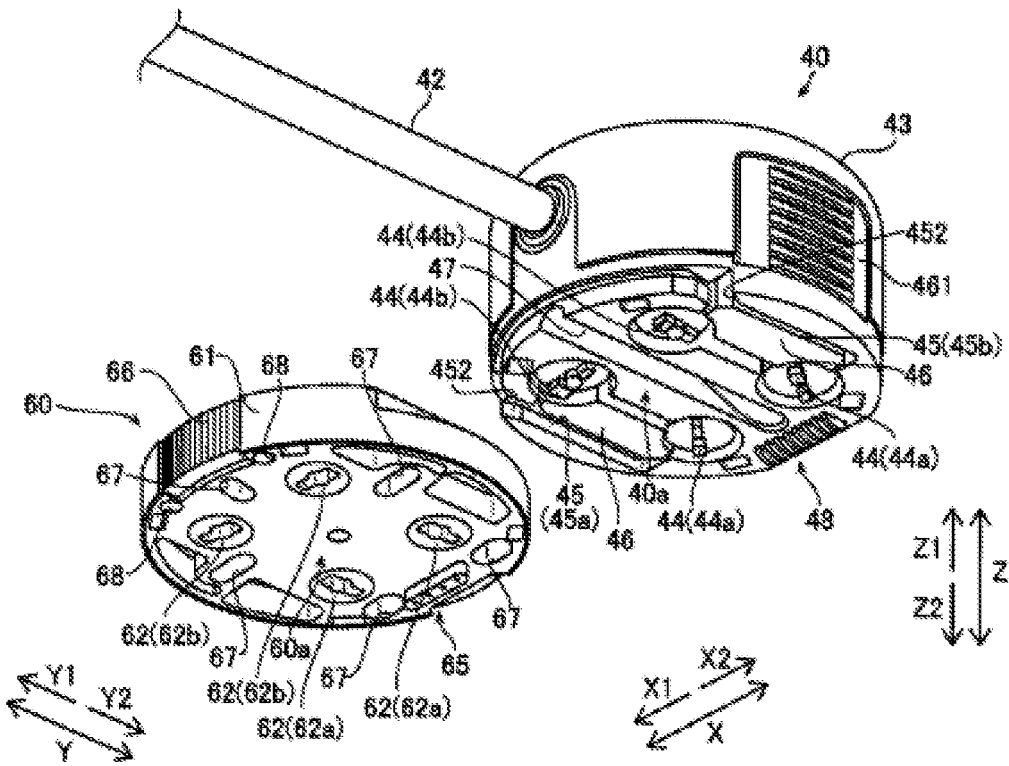
FIG. 5 is a diagram illustrating a perspective view of the adaptor and surgical instrument according to a first embodiment as seen from below.

As illustrated in FIG. 4, the adaptor 60 includes a base body 61, drive transmission members 62, guide rails 63, a precedence guide rail 64, a first electrode array 65, and an arm engagement section 66. As illustrated in FIG. 5, the adaptor 60 includes arm engagement holes 67 and positioning holes 68. As illustrated in FIG. 4, the drive transmission members 62 include first drive transmission members 62a arranged in the Y2 side and second drive transmission members 62b arranged in the Y1 side. In the adaptor 60, a first surface 60a is arranged in the Z2 side and attached to the robot arm 21a. The adaptor 60 includes a second surface 60b arranged in the Z1 side to which the surgical instrument 40 is attached.

As illustrated in FIG. 5, an attachment surface 40a arranged in the Z2 side of the housing 43 of the surgical instrument 40 is attached to the adaptor 60. The surgical instrument 40 includes rotation members 44, two guide grooves 45 (a first guide groove 45a and a second guide groove 45b), two movable members 46, a precedence guide groove 47, and a second electrode array 48. The rotation members 44 include first rotation members 44a arranged in the Y2 side and second rotation members 44b arranged in the Y1 side. The movable members 46 are connected to buttons 461, respectively.

As illustrated in FIG. 4, the drape 70 includes a body section 71 and an attachment section 72. The body section 71 is made in a film form. The attachment section 72 is made by resin molding. The attachment section 72 includes a through-opening in a section where the robot arm 21a is engaged with the adaptor 60. The through-opening may be provided corresponding to the engagement section. Through-openings may be provided corresponding to plural engagement sections.

The adaptor 60 is attached to an adaptor attachment surface 211 of the robot arm 21. The robot arm 21 includes rotation drive sections 212, engagement sections 213, and bosses 214.

As illustrated in FIG. 5, the rotation members 44 of the surgical instrument 40 are rotated and driven and drive the end effector 41. Specifically, the rotation members 44 are connected to the end effector 41 with wires inserted through the shaft 42. When the rotation members 44 are rotated, the wires are pulled and the end effector 41 is driven. The rotation members 44 are connected with the shaft 42 by gears in the housing 43. The shaft 42 is rotated by the rotation of the rotation members 44.

For example, four rotation members 44 are provided. The shaft 42 is rotated by the rotation of one of the rotation members 44, and the end effector 41 is driven by the rotation of the other three rotation members 44. The four rotation members 44 are arranged such that two of them are arranged in the X direction while two of them are arranged in the Y direction.

The guide grooves 45 are provided to extend along the Y direction. The two guide grooves 45 are provided to be opposed to each other in the X direction. The two guide grooves 45 are provided substantially parallel to each other. The two guide rails 63 of the adaptor 60 are respectively inserted into the two guide grooves 45, and the two guide grooves 45 thus guide attachment of the surgical instrument 40 to the adaptor 60. The width of each guide groove 45 is varied according to movement in the X direction of the corresponding movable member 46. Specifically, when the movable member 46 is moved inward, the width of the guide groove 45 is increased. When the movable member 46 is moved outward, the width of the guide groove 45 is decreased. The movable member 46 is biased to a direction (an outward direction) in which the width of the guide groove 45 is decreased. Specifically, the movable member 46 is biased by a spring. When a worker presses the corresponding button 461, the movable member 46 is moved in a direction (an inward direction) in which the width of the guide groove 45 is increased.

The precedence guide groove 47 is provided to extend along the Y direction. The precedence guide groove 47 is provided between the two guide grooves 45 (the first guide groove 45a and the second guide groove 45b). The precedence guide groove 47 is formed to extend substantially parallel to the guide grooves 45. The precedence guide groove 47 is provided in the substantial center in the X direction of the attachment surface 40a.

The second electrode array 48 is connected to the robot arm 21 through the first electrode array 65 of the adaptor 60. The second electrode array 48 is connected to a board provided in the housing 43. Specifically, the board of the surgical instrument 40 is connected to the robot arm 21 by attaching the surgical instrument 40 to the robot arm 21 through the adaptor 60. The board in the housing 43 is used for, for example, managing types of the surgical instrument 40 and the number of uses of the surgical instrument 40.

Figure 6:
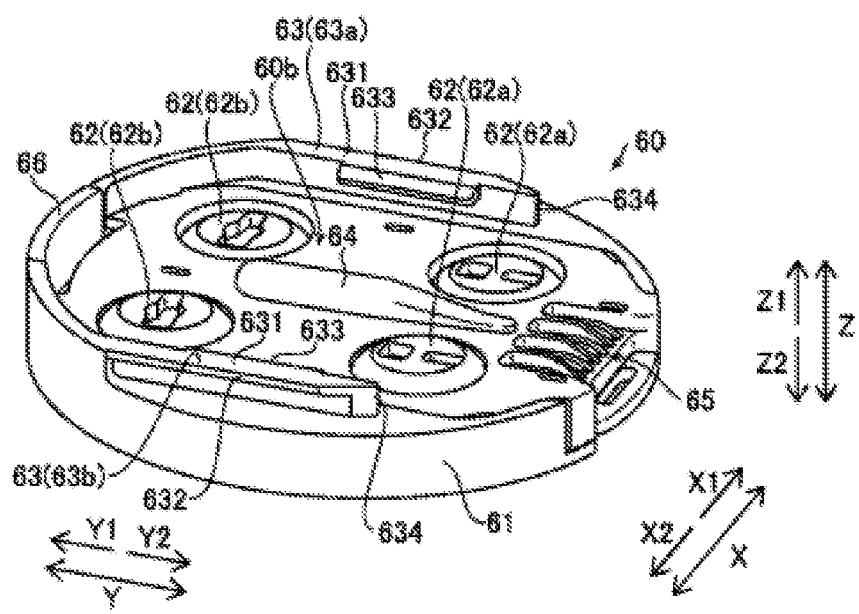
FIG. 6 is a diagram illustrating a perspective view of the adaptor according to a first embodiment as seen from above.

As illustrated in FIGS. 4 to 6, the adaptor 60 is provided to detachably connect the surgical instrument 40 to the robot arm 21a of the robotic surgical system 100. The base body 61 includes the first surface 60a to be attached to the robot arm 21a and the second surface 60b to which the attachment surface 40a of the surgical instrument 40 is mounted. The adaptor 60 has the substantially same size with the housing 43 of the surgical instrument 40 as seen in the Z direction. Specifically, the adaptor 60 is formed in a substantially circular shape having the substantially same diameter as the diameter of the housing 43 as seen in the Z direction.

The drive transmission members 62 are rotatably provided in the base body 61. Specifically, the drive transmission members 62 are provided rotatably about rotation axes extending in the Z direction. The drive transmission members 62 transmit driving force of the rotation drive sections 212 of the robot arm 21a to the rotation members 44 of the surgical instrument 40. Plural drive transmission members 62 are provided corresponding to the rotation members 44 of the surgical instrument 40. The drive transmission members 62 are respectively arranged in positions corresponding to the rotation members 44 of the surgical instrument 40.

The guide rails 63 are provided on the second surface 60b. The guide rails 63 are provided to extend along the Y direction. The two guide rails 63 are provided to be opposed to each other in the X direction. The two guide rails 63 (the first guide rail 63a and the second guide rail 63b) are provided substantially parallel to each other. The first guide rail 63a and the second guide rail 63b are provided correspondingly to the first guide groove 45a and the second guide groove 45b that are provided substantially parallel to each other on the attachment surface 40a of the surgical instrument 40. The first guide rail 63a and the second guide rail 63b of the second surface 60b are configured to make sliding between corresponding one ends 634 (ends in the Y2 side) of the first and second guide rails 63a and 63b and one ends 452 (ends in the Y1 side) of the first and second guide grooves 45a and 45b of the attachment surface 40a and guide the surgical instrument 40 such that the drive transmission members 62 correspond to the rotation members 44 provided on the attachment surface 40a.

The first guide rail 63a and the second guide rail 63b can be formed on the second surface 60b on which the attachment surface 40a of the surgical instrument 40 is mounted, such that the guide rails 63 correspond to the guide grooves 45 of the attachment surface 40a of the surgical instrument 40. Then, the first guide rail 63a and the second guide rail 63b can be formed in inner sides with respect to the attachment surface 40a of the surgical instrument 40 in plan view (as seen in the Z direction). Consequently, the adaptor 60 can be formed smaller than the attachment surface 40a of the surgical instrument 40, and thus it is possible to downsize the adaptor 60 that detachably connects the surgical instrument 40 to the robot arm 21a of the robotic surgical system 100.

The first guide rail 63a and the second guide rail 63b are configured to guide the first guide groove 45a and the second guide groove 45b of the surgical instrument 40 in a direction (the Y direction) crossing a direction (the Z direction) in which a second member 622 moves with respect to a first member 621. Specifically, a direction in which the surgical instrument 40 is slid and inserted into the adaptor 60 is substantially parallel to a direction in which the shaft 42 of the surgical instrument 40 extends. Unlike in a case where the slide insertion direction crosses the shaft 42-extending direction, a space for moving the shaft 42 required when sliding and attaching/detaching the surgical instrument 40 with respect to the adaptor 60 may only be provided in the shaft 42-extending direction. Specifically, there is no need to provide a large space for moving the shaft 42 in the direction crossing the shaft 42-extending direction.

The precedence guide rail 64 is provided on the second surface 60b. The precedence guide rail 64 is provided to extend along the Y direction. The precedence guide rail 64 is provided between the first guide rail 63a and the second guide rail 63b. The precedence guide rail 64 is formed to extend substantially parallel to the first guide rail 63a and the second guide rail 63b. The precedence guide rail 64 is provided in the substantial center in the X direction of the second surface 60b. The precedence guide rail 64 is provided correspondingly to the precedence guide groove 47 provided on the attachment surface 40a. Specifically, the precedence guide rail 64 guides the surgical instrument 40 before the first guide rail 63a and the second guide rail 63b guide the surgical instrument 40. The first guide rail 63a and the second guide rail 63b can be guided easily to the first guide groove 45a and the second guide groove 45b by the guiding by the precedence guide rail 64 provided between the first guide rail 63a and the second guide rail 63b. This makes it possible to attach the surgical instrument 40 to the adaptor 60 easily.

A section of the precedence guide rail 64 in the upstream side (the Y2 side) in a slide insertion direction in which the surgical instrument 40 is slid and inserted into the adaptor 60 is formed in a tapered shape. Specifically, the precedence guide rail 64 is formed such that an end section at the trailing side (the Y2 side) in the slide insertion direction has a width tapered in the X direction. The precedence guide rail 64 is formed such that the end section in the Y2 side has a height tapered in the Z direction. Such a tapered section makes it possible to guide the precedence guide rail 64 to the precedence guide groove 47 easily.

Figure 8:
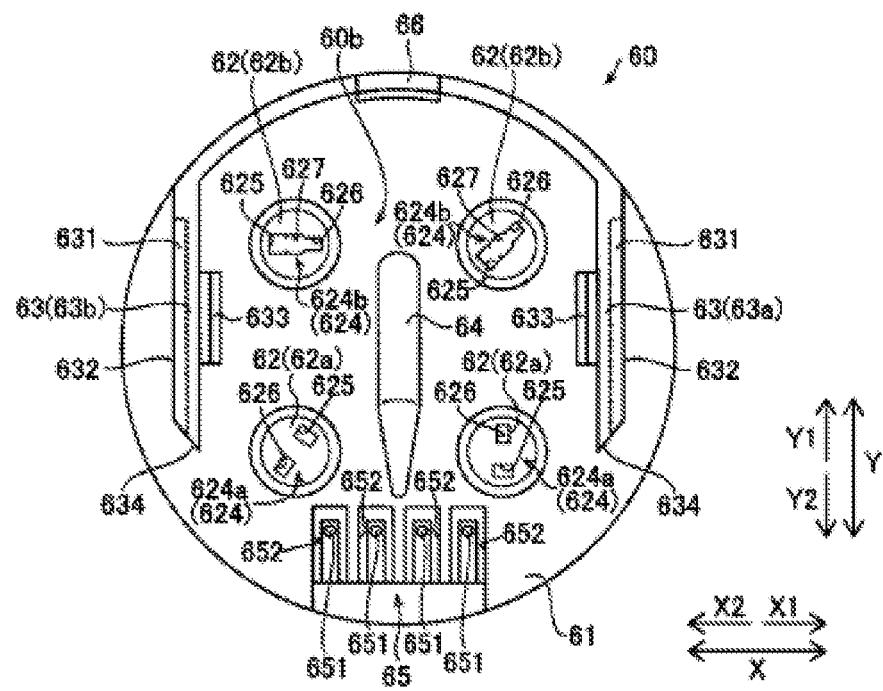
FIG. 8 is a diagram illustrating a plan view of the adaptor according to a first embodiment.

The first electrode array 65 is connected to the second electrode array 48 of the surgical instrument 40 and the robot arm 21. As illustrated in FIG. 8, the first electrode array 65 includes electrodes 651 and grooves 652. The electrodes 651 are arranged to extend in the Z direction and penetrate the base body 61. The grooves 652 are provided on the second surface 60b. The grooves 652 receive protrusions 482 (see FIG. 11) provided in the second electrode array 48 on the attachment surface 40a of the surgical instrument 40. Specifically, when the surgical instrument 40 is attached to the adaptor 60, the protrusions 482 are fitted in the grooves 652. Even when the surgical instrument 40 is detached from the adaptor 60, the protrusions 482 and the grooves 652 can prevent the worker from touching the first electrode array 65 and the second electrode array 48. Additionally, the first electrode array 65 and the second electrode array 48 can be connected with each other by fitting the protrusions 482 in the grooves 652 when attaching the surgical instrument 40 to the adaptor 60.

The arm engagement section 66 is engaged with the engagement sections 213 of the robot arm 21. Specifically, the arm engagement section 66 is engaged with the engagement sections 213 that are inserted in the arm engagement holes 67 provided in the first surface 60a. The arm engagement section 66 can be moved in the Y direction. The arm engagement section 66 is biased in the Y1 direction by a bias member. The engagement of the arm engagement section 66 with the engagement sections 213 is made by moving the arm engagement section 66 in the Y1 direction. On the other hand, the engagement of the arm engagement section 66 with the engagement sections 213 is released by moving the arm engagement section 66 in the Y2 direction.

Plural arm engagement holes 67 are provided. Specifically, the adaptor 60 is fixed to the robot arm 21 by engagement of plural sections. For example, five arm engagement holes 67 are provided. The arm engagement holes 67 are provided at equal intervals along a circumferential direction of the first surface 60a.

The positioning holes 68 are provided in the first surface 60a. The bosses 214 of the robot arm 21 are fitted to the positioning holes 68. Plural positioning holes 68 are provided. The positioning holes 68 are provided near an end section in the Y1 side of the first surface 60a.

Figure 7:
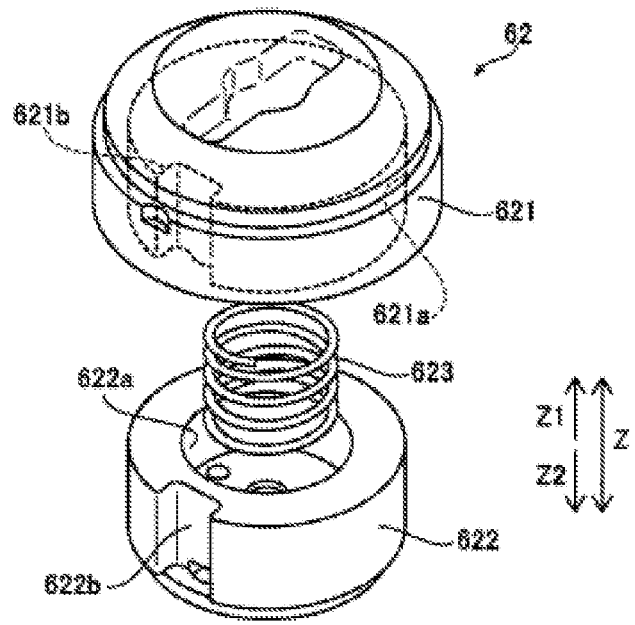
FIG. 7 is a diagram illustrating an exploded perspective view of a drive transmission member of the adaptor according to a first embodiment.

As illustrated in FIG. 7, each drive transmission member 62 includes the first member 621 and the second member 622. The second member 622 is provided movably with respect to the first member 621 with a bias member 623 interposed in between. The first member 621 includes a recess section 621a and an engagement section 621b. The recess section 621a receives the second member 622 fitted thereto. The engagement section 621b is engaged with the second member 622. The second member 622 includes a recess section 622a and an engagement section 622b. The recess section 622a houses the bias member 623. The engagement section 622b is engaged with the first member 621. The first member 621 and the second member 622 are fitted to each other in the Z direction with the bias member 623 interposed in between. The first member 621 is positioned in the second surface 60b side (the Z1 side). The second member 622 is positioned in the first surface 60a side (the Z2 side). The bias member 623 biases the first member 621 toward the Z1 side with respect to the second member 622. For example, a spring constitutes the bias member 623.

The second member 622 is arranged flush with the first surface 60a in the Z direction. The second member 622 is arranged so as not to move with respect to the base body 61 in the Z direction. The first member 621 is arranged movably with respect to the base body 61 in the Z direction. This makes it possible to move the first member 621 of the drive transmission member 62 downward in the Z direction to prevent interference with the movement of the surgical instrument 40 when attaching the surgical instrument 40 to the adaptor 60 by the guiding along the first guide rail 63a and the second guide rail 63b.

The first member 621 is configured to rotate in accordance with the rotation of the second member 622 about the rotation axis in the Z direction. Specifically, the first member 621 is configured such that the engagement section 621b provided in an inner circumferential section of the first member 621 and the engagement section 622b provided in an outer circumferential section of the second member 622 are engaged with each other. The engagement section 621b of the first member 621 is formed to protrude inward from the recess section 621a. The engagement section 622b of the second member 622 is formed to be recessed inward from the outer circumferential section of the second member 622. The engagement section 621b of the first member 621 and the engagement section 622b of the second member 622 are configured to be engaged with each other even when the first member 621 is moved with respect to the second member 622 in the Z direction. Specifically, the first member 621 is configured to be rotated with the second member 622 regardless of a location of the first member 621 with respect to the second member 622 in the Z direction. When the second member 622 is rotated in accordance with the rotation of the rotation drive section 212 of the robot arm 21, the first member 621 is rotated together. Consequently, the rotation of the rotation drive section 212 of the robot arm 21 is transmitted to the rotation member 44 of the surgical instrument 40 engaged with the first member 621.

Figure 9:
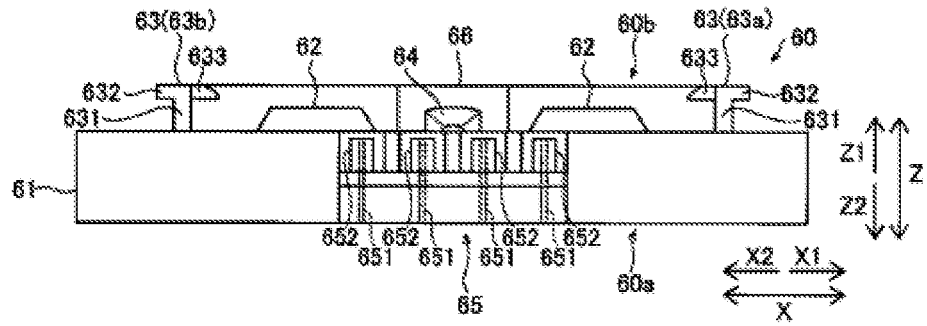
FIG. 9 is a diagram illustrating a front view of the adaptor according to a first embodiment.

As illustrated in FIGS. 8 and 9, each guide rail 63 includes a rail section 631, a jut section 632, and a tab section 633. The rail section 631 is formed to extend in the Y direction. The rail section 631 slides into the guide groove 45 of the surgical instrument 40 and guides the movement of the surgical instrument 40 with respect to the adaptor 60.

The jut section 632 is formed to jut in the X direction from the rail section 631. Specifically, the jut section 632, which is included in the first guide rail 63a, one of the guide rails 63 in the X1 side, is arranged in the X1 side of the rail section 631. The jut section 632, which is included in the second guide rail 63b, one of the guide rails 63 in the X2 side, is arranged in the X2 side of the rail section 631.

The tab section 633 is formed to jut in the X direction from the rail section 631. Specifically, the tab section 633, which is included in the first guide rail 63a, one of the guide rails 63 in the X1 side, is arranged in the X2 side of the rail section 631. The tab section 633, which is included in the second guide rail 63b, one of the guide rails 63 in the X2 side, is arranged in the X1 side of the rail section 631. Specifically, the jut section 632 is provided to the rail section 631 on the opposite side of the tab section 633. The jut section 632 is arranged in the outer side in the X direction of the rail section 631. The tab section 633 is arranged in the inner side in the X direction of the rail section 631.

The jut section 632 is engaged with an engagement groove 451 (see FIGS. 10 and 11) provided in the guide groove 45 of the surgical instrument 40. The engagement of the jut section 632 with the engagement groove 451 makes it possible to fix the surgical instrument 40 to the adaptor 60 more stably. Specifically, the engagement of the jut section 632 with the engagement groove 451 enables rigid connection between the surgical instrument 40 and the adaptor 60 and prevents detachment of the surgical instrument 40 from the adaptor 60 in the Z direction.

The tab section 633 is engaged with an engagement hole 462 (see FIGS. 10 and 11) provided in the guide groove 45 of the surgical instrument 40. Specifically, the tab section 633 is engaged with the engagement hole 462 provided in a side wall of the movable member 46 forming the guide groove 45. The engagement of the tab section 633 with the engagement hole 462 enables positioning and fixing of the surgical instrument 40 guided by the guide rail 63 with respect to the adaptor 60. Specifically, the engagement of the tab section 633 with the engagement hole 462 enables positioning of the surgical instrument 40 in the Y direction with respect to the adaptor 60 and fixing (locking) of the surgical instrument 40 to the adaptor 60 to prevent detachment of the surgical instrument 40 in the Y direction. As illustrated in FIG. 9, the tab section 633 is formed to be inclined along the X direction.

As illustrated in FIG. 8, the drive transmission members 62 respectively include engagement sections 624 engaged with the corresponding rotation members 44 provided on the attachment surface 40a of the surgical instrument 40. The engagement sections 624 include a first engagement section 624a and a second engagement section 624b. The first engagement section 624a is provided in the first drive transmission member 62a of the drive transmission members 62 located on the upstream side in the slide insertion direction (the Y2 side). The second engagement section 624b is provided in the second drive transmission member 62b of the drive transmission members 62 located on a downstream side in the slide insertion direction (the Y1 side). The first engagement section 624a and the second engagement section 624b have different shapes. This makes it possible to prevent the first drive transmission member 62a from being engaged and stuck with the rotation member 44 corresponding to the second drive transmission member 62b during the sliding of the surgical instrument 40 with respect to the adaptor 60. Thus, it is possible to attach the surgical instrument 40 to the adaptor 60 smoothly.

Specifically, the first engagement section 624a has a shape that avoids the engagement with the rotation member 44 that is engaged with the second engagement section 624b. This makes it possible to more reliably prevent the first drive transmission member 62a from being engaged and stuck with the rotation member 44 corresponding to the second drive transmission member 62b during the sliding of the surgical instrument 40 with respect to the adaptor 60.

Figure 10:
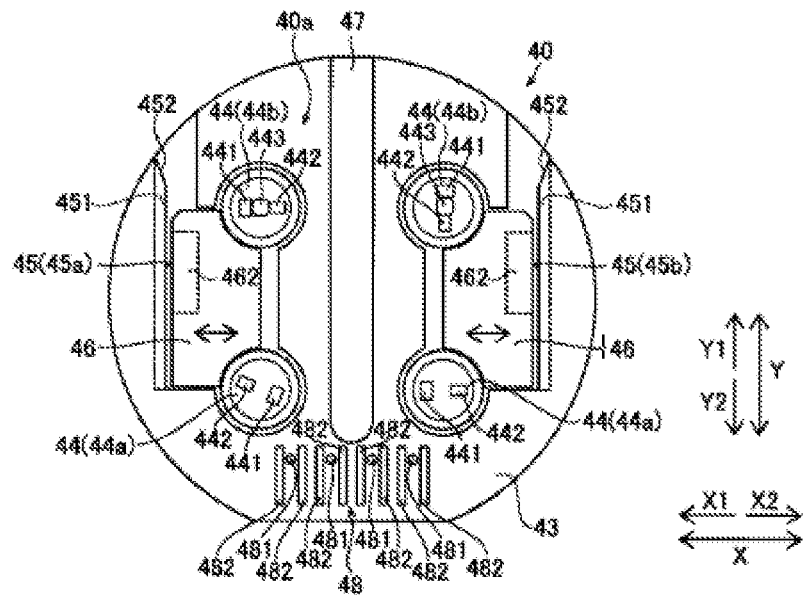
FIG. 10 is a diagram illustrating a bottom view of a base body of the surgical instrument according to a first embodiment.

Specifically, in the second surface 60b side of the first drive transmission member 62a, a first recess 625 and a second recess 626 are separately formed as the first engagement section 624a. In the second surface 60b side of the second drive transmission member 62b, one recess in which the first recess 625 and the second recess 626 are connected with each other by a third recess 627 is formed as the second engagement section 624b. As illustrated in FIG. 10, the first rotation member 44a, which is one of the rotation members 44 provided on the attachment surface 40a of the surgical instrument 40 and is engaged with the first drive transmission member 62a, includes a first projection 441 and a second projection 442 inserted into the first recess 625 and the second recess 626. Specifically, the first projection 441 is engaged with the first recess 625, and the second projection 442 is engaged with the second recess 626.

The second rotation member 44b, which is one of the rotation members 44 provided on the attachment surface 40a of the surgical instrument 40 and is engaged with the second drive transmission member 62b, includes the first projection 441, the second projection 442, and a third projection 443 arranged between the first projection 441 and the second projection 442, which are inserted together into the one recess. Specifically, the first projection 441 is engaged with the first recess 625, the second projection 442 is engaged with the second recess 626, and the third projection 443 is engaged with the third recess 627. As the first recess 625 and the second recess 626 are independently provided or the first recess 625 and the second recess 626 are connected and form the one recess, the first engagement section 624a and the second engagement section 624b can be formed in different shapes easily. Since the parts constituting the first projection 441 and the second projection 442 are common, the engagement sections of the first rotation members 44a and the second rotation members 44b can be formed in different shapes depending on only whether there is the third projection 443. Thus, it is possible to reduce increase of parts types.

Figure 11:
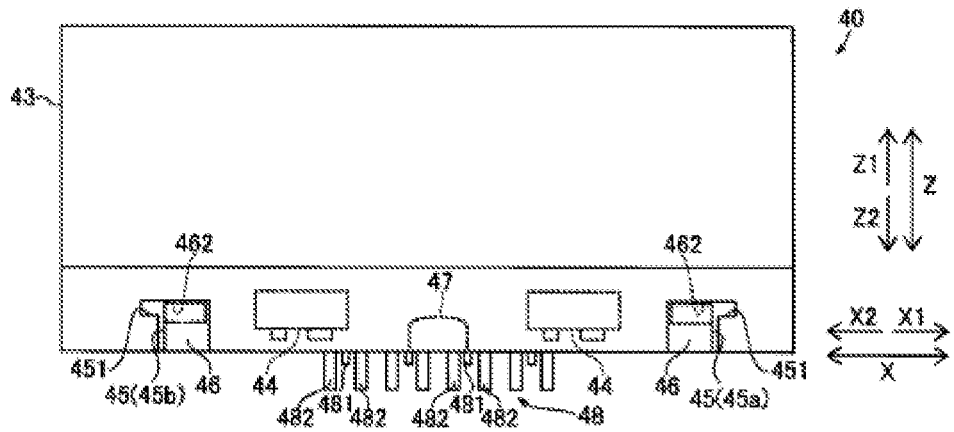
FIG. 11 is a diagram illustrating a front view of the base body of the surgical instrument according to a first embodiment.

As illustrated in FIGS. 10 and 11, the engagement groove 451 is provided in the guide groove 45 of the attachment surface 40a of the surgical instrument 40. The engagement groove 451 is formed to extend in the Y direction along the guide groove 45. The jut section 632 of the guide rail 63 provided on the second surface 60b of the adaptor 60 is engaged with the engagement groove 451.

The engagement hole 462 is provided in the side wall of the movable member 46 forming the guide groove 45. The tab section 633 of the guide rail 63 provided on the second surface 60b of the adaptor 60 is engaged with the engagement hole 462. The engagement of the tab section 633 with the engagement hole 462 is released by moving the movable member 46 inward in the X direction. The engagement of the drive transmission member 62 with the rotation member 44 is released by moving the movable member 46 inward in the X direction and pushing the drive transmission member 62 in the Z2 direction. In this state, the surgical instrument 40 can be detached from the adaptor 60 by sliding the surgical instrument 40 in the Y2 direction with respect to the adaptor 60.

The second electrode array 48 on the attachment surface 40a of the surgical instrument 40 includes electrodes 481 and the protrusions 482. The electrodes 481 are respectively connected with the electrodes 651 of the first electrode array 65 of the adaptor 60. The protrusions 482 are located in two sides in the X direction of each electrode 481. The protrusions 482 are provided for preventing hand touch on the electrode 481. Specifically, an interval between the protrusions 482 sandwiching the electrode 481 is sufficiently smaller than the finger size. The protrusion 482 protrudes in the Z direction more than the electrode 481 does.

(Attachment of Surgical Instrument to Robot Arm)

Figure 12:
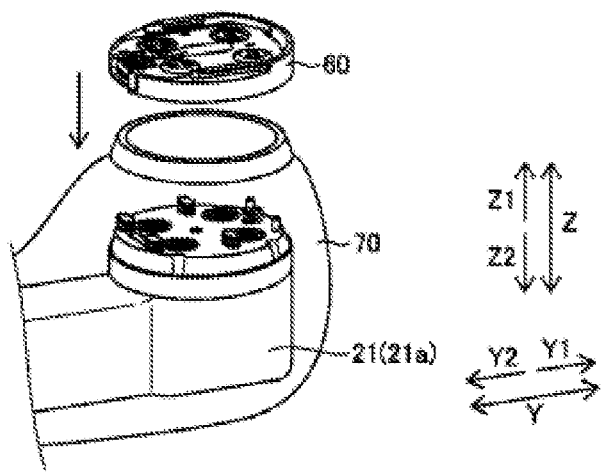
FIG. 12 is a diagram illustrating an explanatory view of attachment of the adaptor to the robot arm according to a first embodiment.
Figure 13:
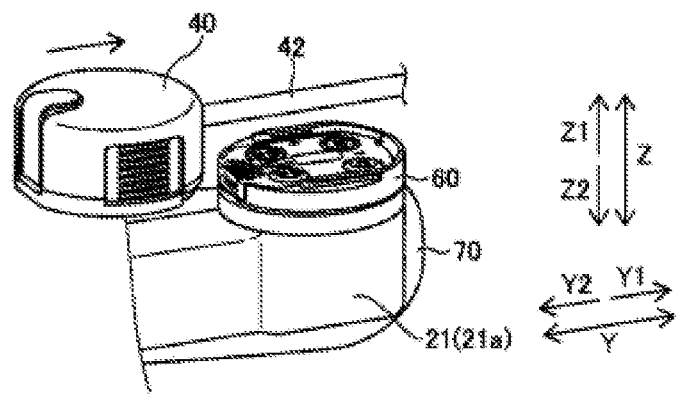
FIG. 13 is a diagram illustrating a first explanatory view of attachment of the surgical instrument to the adaptor according to a first embodiment.
Figure 14:
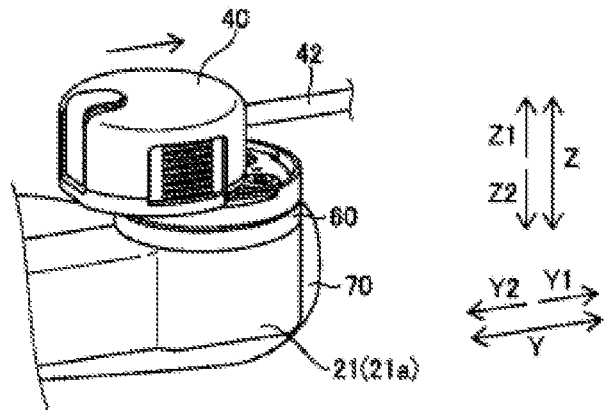
FIG. 14 is a diagram illustrating a second explanatory view of attachment of the surgical instrument to the adaptor according to a first embodiment.

With reference to FIGS. 12 to 14, attachment of the surgical instrument 40 to the robot arm 21a according to a first embodiment is described.

As illustrated in FIG. 12, the adaptor 60 is attached to the robot arm 21a covered by the drape 70. The adaptor 60 is moved in the Z direction with respect to the robot arm 21a to be attached to the robot arm 21a. As illustrated in FIGS. 13 and 14, the surgical instrument 40 is attached to the adaptor 60 attached to the robot arm 21a. The surgical instrument 40 is slid and moved in the slide insertion direction (the Y1 direction) along the precedence guide rail 64, the first guide rail 63a, and the second guide rail 63b of the adaptor 60 and thereby attached to the adaptor 60. In this way, the surgical instrument 40 is attached to the robot arm 21a through the adaptor 60.

When detaching the surgical instrument 40 from the robot arm 21a, the surgical instrument 40 is slid and moved in the opposite direction (the Y2 direction) of the slide insertion direction while pressing the button 461 of the movable member 46 of the surgical instrument 40 and then detached from the adaptor 60.

Second Embodiment

Next, with reference to FIGS. 15 to 26, a second embodiment of the disclosure is described. In a second embodiment, an example of a configuration in which the adaptor of a first embodiment is further provided with precedence guide sections is described.

Figure 15:
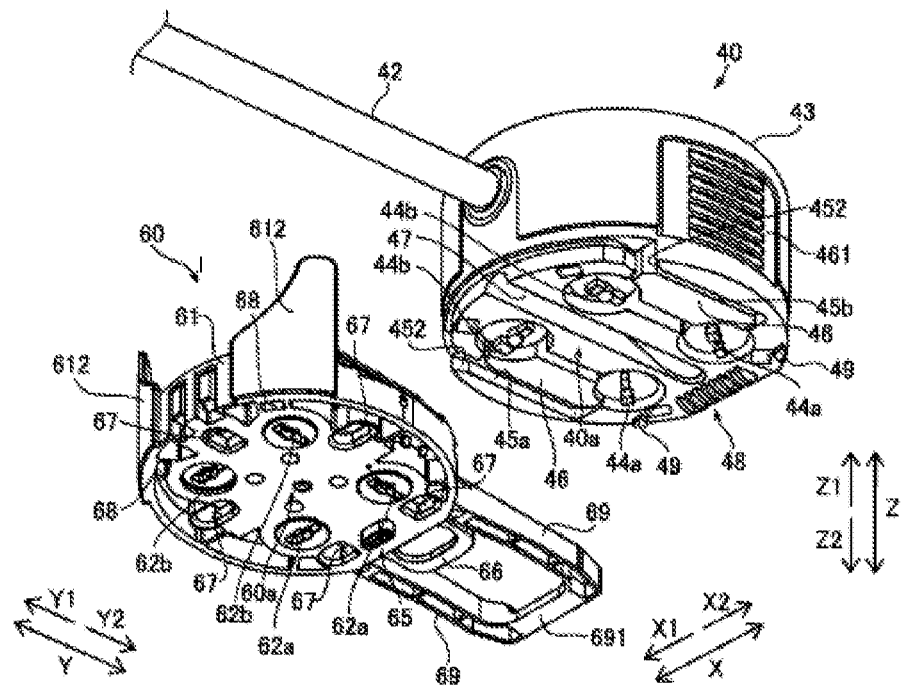
FIG. 15 is a diagram illustrating a perspective view of an adaptor and a surgical instrument according to a second embodiment as seen from below.
Figure 16:
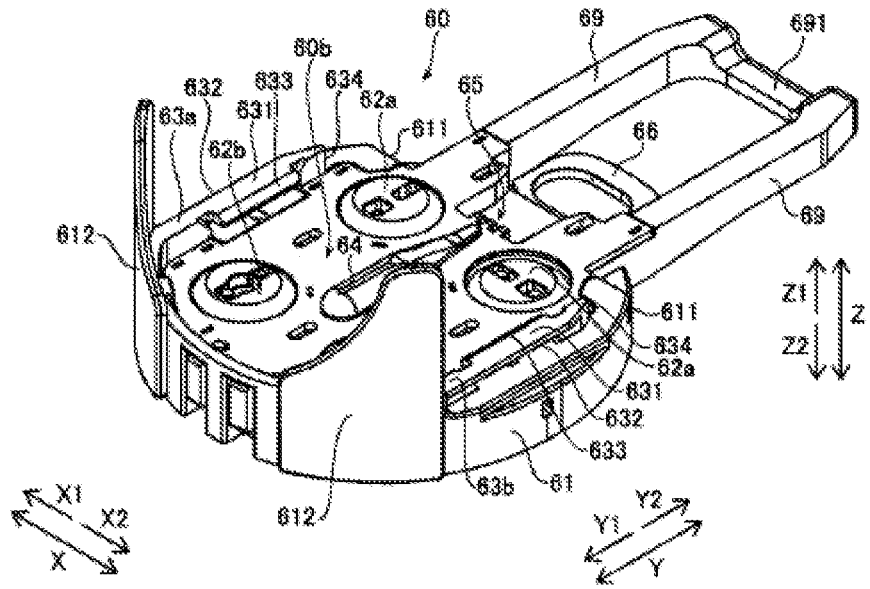
FIG. 16 is a diagram illustrating a perspective view of the adaptor according to a second embodiment as seen from above.

As illustrated in FIGS. 15 and 16, the adaptor 60 of a second embodiment is provided with precedence guide sections 69. The precedence guide sections 69 are formed to protrude from the base body 61 along a direction (the Y direction) parallel to a direction in which the first guide rail 63a and the second guide rail 63b extend. The precedence guide sections 69 guides the surgical instrument 40 before the first guide rail 63a and the second guide rail 63b guide the surgical instrument 40. The first guide rail 63a and the second guide rail 63b can be guided easily to the first guide groove 45a and the second guide groove 45b by the guiding by the precedence guide sections 69 provided to protrude from the base body 61. This makes it possible to attach the surgical instrument 40 to the adaptor 60 easily. The precedence guide sections 69 provided to protrude from the base body 61 enable easy recognition of an attachment direction and attachment position of the surgical instrument 40 with respect to the adaptor 60.

Each precedence guide section 69 is configured to guide a protrusion 49 in the direction (the Y direction) in which the first guide rail 63a and the second guide rail 63b extend, the protrusion 49 protruding from the attachment surface 40a of the surgical instrument 40 toward the second surface 60b. The sliding of the protrusion 49 provided on the attachment surface 40a of the surgical instrument 40 along the precedence guide section 69 makes it possible to easily guide the surgical instrument 40 to an attachment position of the adaptor 60.

As illustrated in FIG. 15, a pair of the protrusions 49 of the surgical instrument 40 are provided near an end section in the Y2 direction of the attachment surface 40a. The pair of protrusions 49 are arranged at a predetermined interval in the X direction. The pair of protrusions 49 are arranged so as to sandwich the second electrode array 48.

The second surface 60b of the base body 61 includes attachment engagement sections 611 with which the protrusions 49 of the attachment surface 40a are engaged. Since the protrusions 49 to be engaged with the attachment engagement sections 611 can be guided by the precedence guide sections 69, there is no need to additionally provide a guiding member in the surgical instrument. Specifically, as illustrated in FIG. 16, a pair of the attachment engagement sections 611 are provided near an end section in the Y2 direction of the second surface 60b of the base body 61. The pair of attachment engagement sections 611 are arranged at a predetermined interval in the X direction. The pair of attachment engagement sections 611 are arranged so as to sandwich the first electrode array 65.

Figure 24:
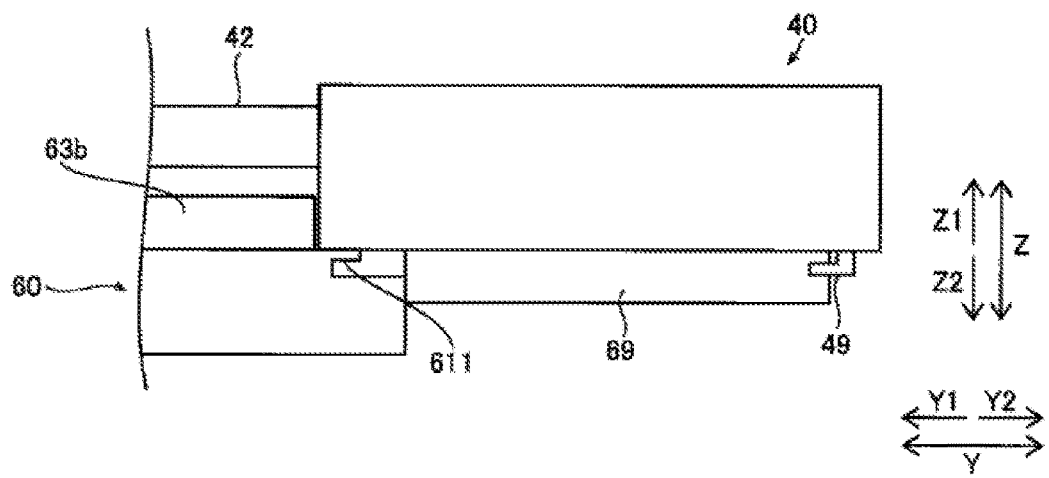
FIG. 24 is a diagram illustrating a first explanatory side view of attachment of the surgical instrument to the adaptor according to a second embodiment.
Figure 25:
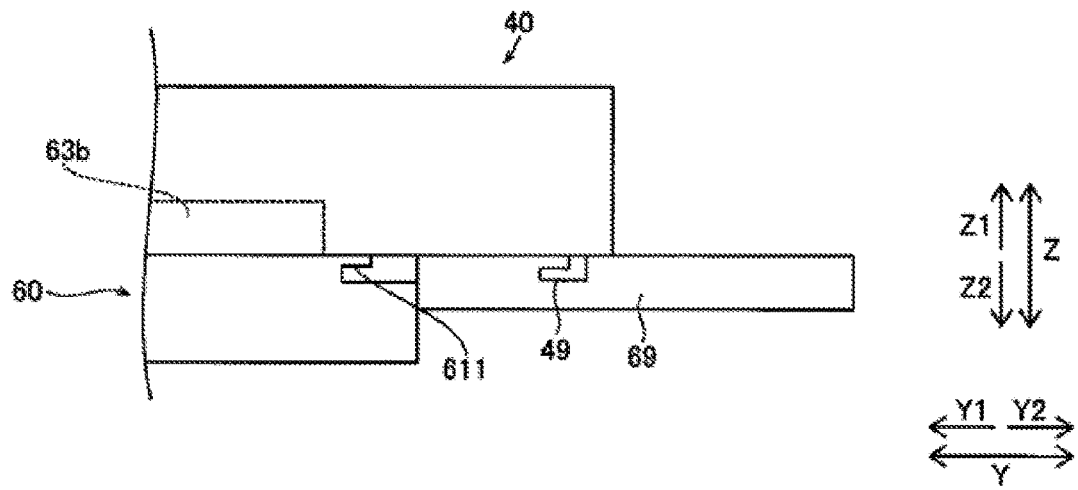
FIG. 25 is a diagram illustrating a second explanatory side view of attachment of the surgical instrument to the adaptor according to a second embodiment.
Figure 26:
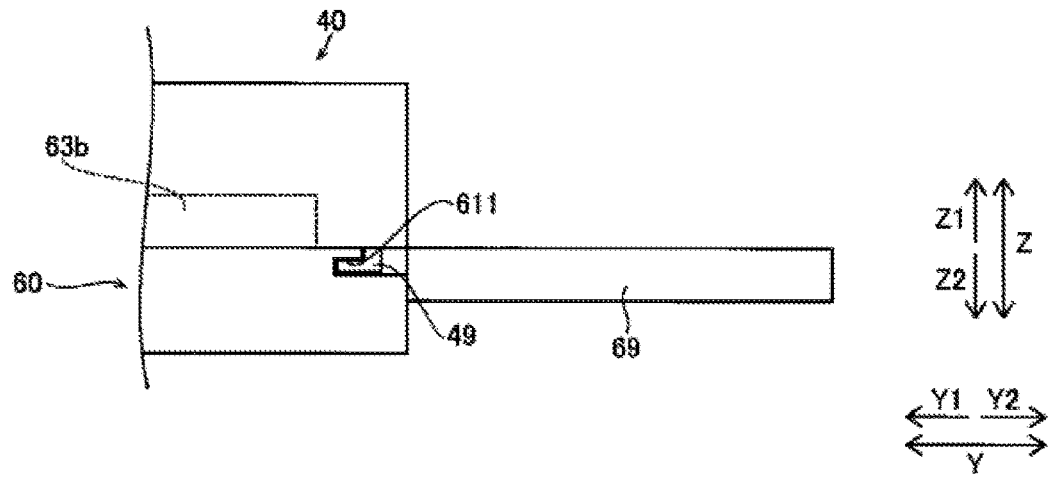
FIG. 26 is a diagram illustrating a third explanatory side view of attachment of the surgical instrument to the adaptor according to a second embodiment.

As illustrated in FIGS. 24 to 26, each attachment engagement section 611 in side view includes a recess that is recessed in the Y direction. Each protrusion 49 in side view includes a protrusion protruding in the Y direction. With the protrusion of the protrusion 49 fitted in the recess section of the attachment engagement section 611, the protrusion 49 and the attachment engagement section 611 are engaged with each other.

As illustrated in FIG. 16, in a second embodiment, the base body 61 is provided with contact sections 612 with which the surgical instrument 40 comes into contact. A pair of the contact sections 612 are provided near an end section in the Y1 direction of the second surface 60b of the base body 61. The pair of contact sections 612 are arranged at a predetermined interval in the X direction. The pair of contact sections 612 are formed to protrude toward the surgical instrument 40 (the Z1 side). The contact sections 612 are configured to come into contact with an end section in the Y1 side of the housing 43 of the surgical instrument 40 when the surgical instrument 40 is attached to the adaptor 60.

A pair of the precedence guide sections 69 are provided substantially in parallel to the first surface 60a and the second surface 60b and substantially in parallel to each other at a predetermined interval in a direction (the X direction) orthogonal to a direction in which the surgical instrument 40 is guided (a direction parallel to the slide insertion direction). The surgical instrument 40 can be guided to the attachment position of the adaptor 60 more stably than a case where the surgical instrument 40 is guided by only one precedence guide section 69.

Figure 21:
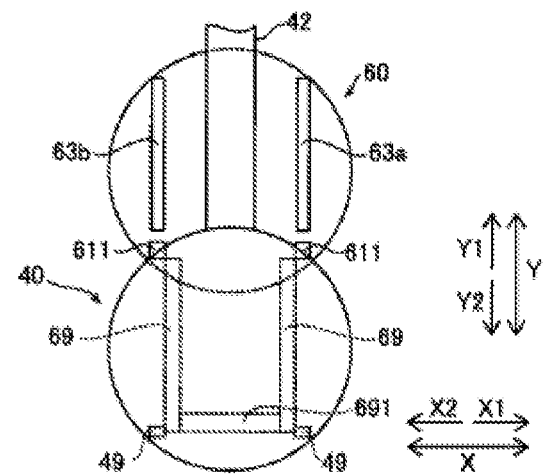
FIG. 21 is a diagram illustrating a first explanatory plan view of attachment of the surgical instrument to the adaptor according to a second embodiment.
Figure 22:
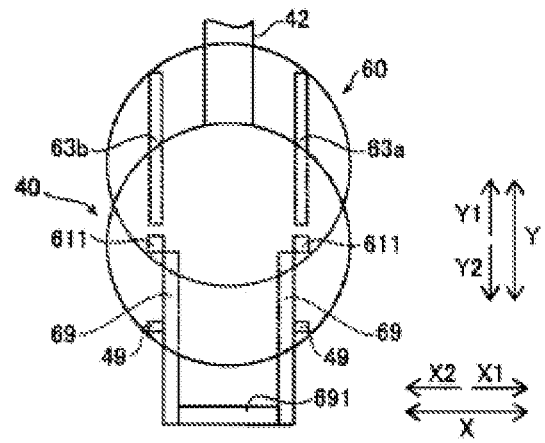
FIG. 22 is a diagram illustrating a second explanatory plan view of attachment of the surgical instrument to the adaptor according to a second embodiment.
Figure 23:
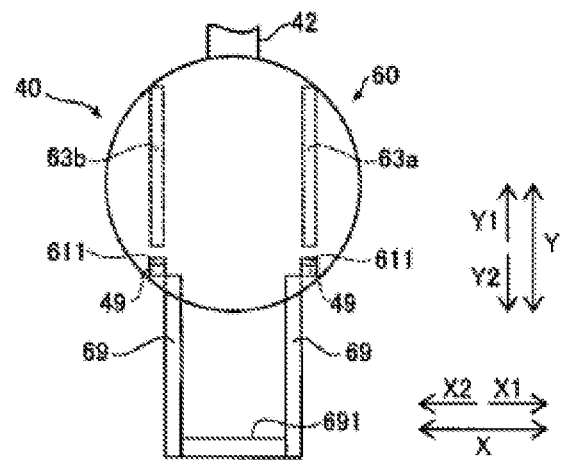
FIG. 23 is a diagram illustrating a third explanatory plan view of attachment of the surgical instrument to the adaptor according to a second embodiment.

As illustrated in FIGS. 21 to 23, the pair of precedence guide sections 69 are configured to respectively guide the protrusions 49 of the surgical instrument 40 using outer surfaces in the X direction. Specifically, the precedence guide section 69 in the X1 direction side guides the protrusion 49 of the surgical instrument 40 in the Y direction using a side surface in the X1 direction side, and the precedence guide section 69 in the X2 direction side guides the protrusion 49 of the surgical instrument 40 in the Y direction using a side surface in the X2 direction side.

As illustrated in FIG. 16, end sections of the pair of precedence guide sections 69 on the upstream side in the slide insertion direction (the Y2 side) are connected to each other by a connection section 691. The connection of the end sections of the pair of precedence guide sections 69 can improve the mechanical strength of the pair of precedence guide sections 69 and thereby can suppress the deformation due to bending of the pair of precedence guide sections 69. This makes it possible to reliably exert the guiding function of the pair of precedence guide sections 69.

The connection section 691 is formed to extend in a direction (the X direction) in which the pair of precedence guide sections 69 are arranged side by side. The connection section 691 is formed such that a side in the surgical instrument 40 side (the Z1 side) is recessed. This can reduce the interference with the connection section 691 from the second electrode array 48 protruding in the Z2 direction from the attachment surface 40a of the surgical instrument 40 when the surgical instrument 40 is guided by the precedence guide sections 69 and slid in the Y1 direction. The pair of precedence guide sections 69 and the connection section 691 are formed integrally. This can reduce the number of parts more than a case where the pair of precedence guide sections 69 and the connection section 691 are formed separately.

In a second embodiment, the first guide rail 63a and the second guide rail 63b of the second surface 60b are configured to make sliding between the corresponding one ends 634 (the ends in the Y2 side) of the first and second guide rails 63a and 63b and one ends 452 (the ends in the Y1 side) of the first and second guide grooves 45a and 45b of the attachment surface 40a and guide the surgical instrument 40 such that the drive transmission members 62 correspond to the rotation members 44 provided on the attachment surface 40a.

(Attachment of Surgical Instrument to Robot Arm)

With reference to FIGS. 17 to 20, attachment of the surgical instrument 40 to the robot arm 21a according to a second embodiment is described.

Figure 17:
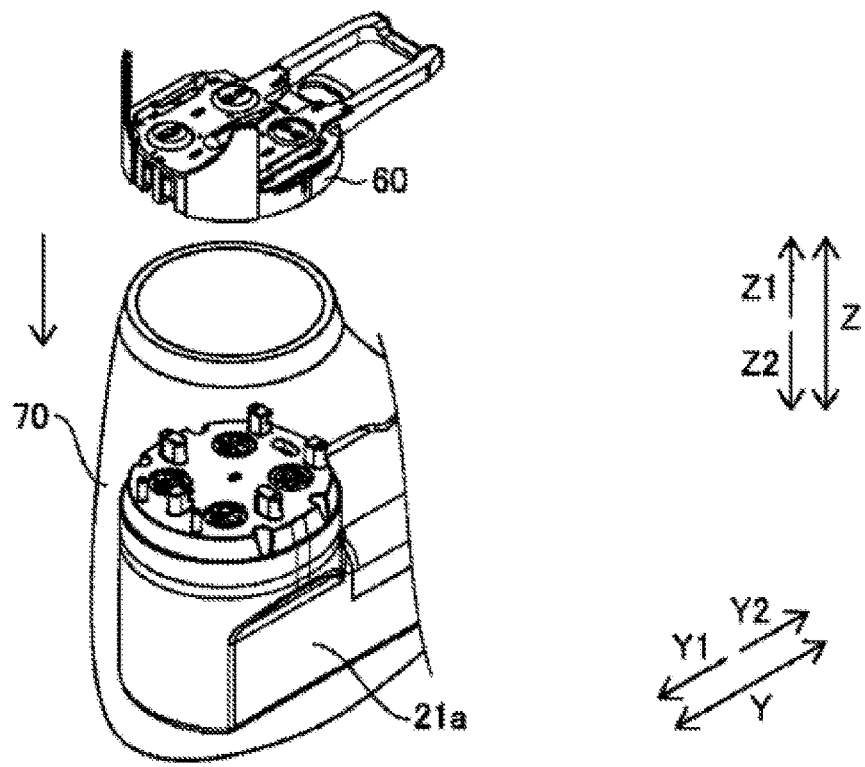
FIG. 17 is a diagram illustrating an explanatory perspective view of attachment of the adaptor to a robot arm according to a second embodiment.
Figure 18:
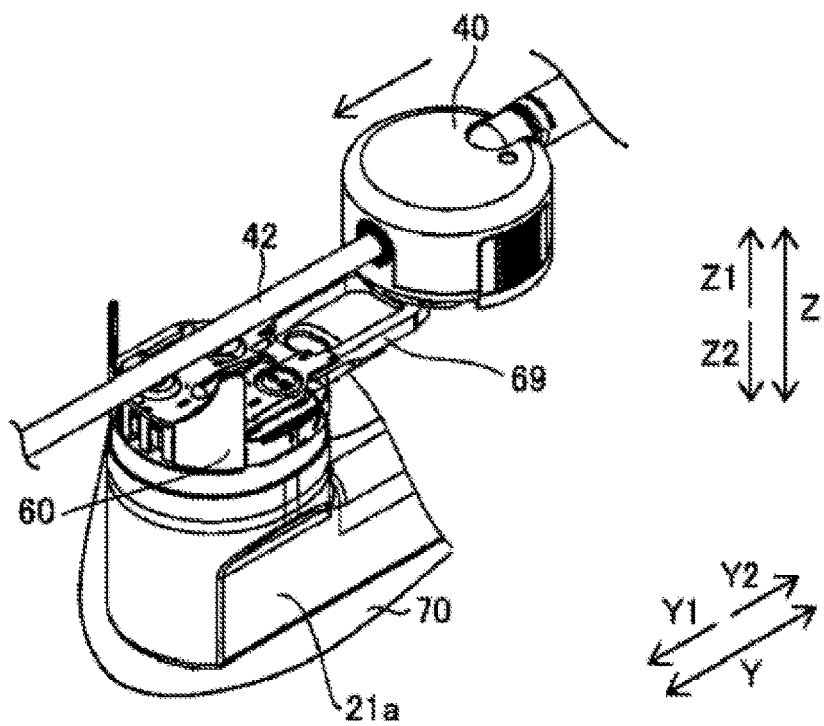
FIG. 18 is a diagram illustrating a first explanatory perspective view of attachment of the surgical instrument to the adaptor according to a second embodiment.
Figure 19:
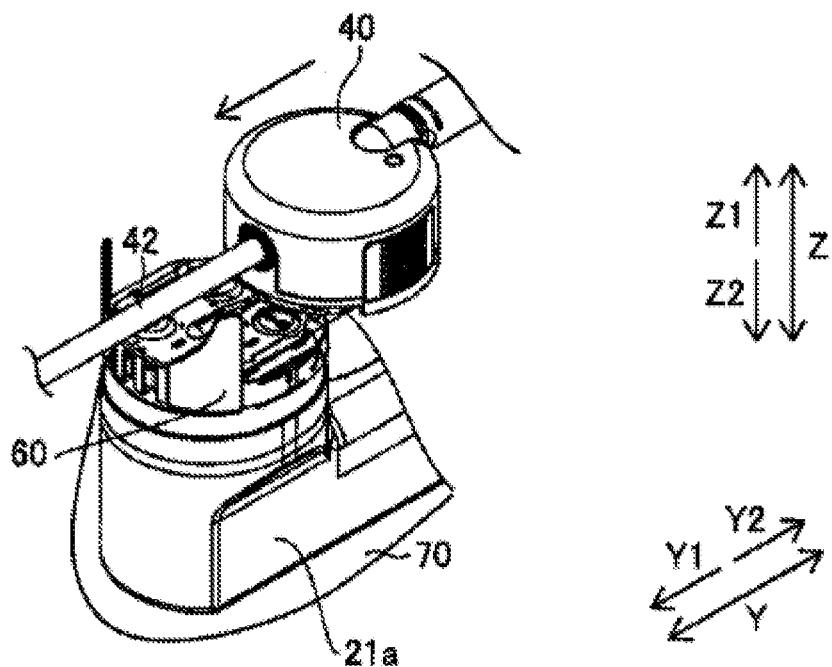
FIG. 19 is a diagram illustrating a second explanatory perspective view of attachment of the surgical instrument to the adaptor according to a second embodiment.
Figure 20:
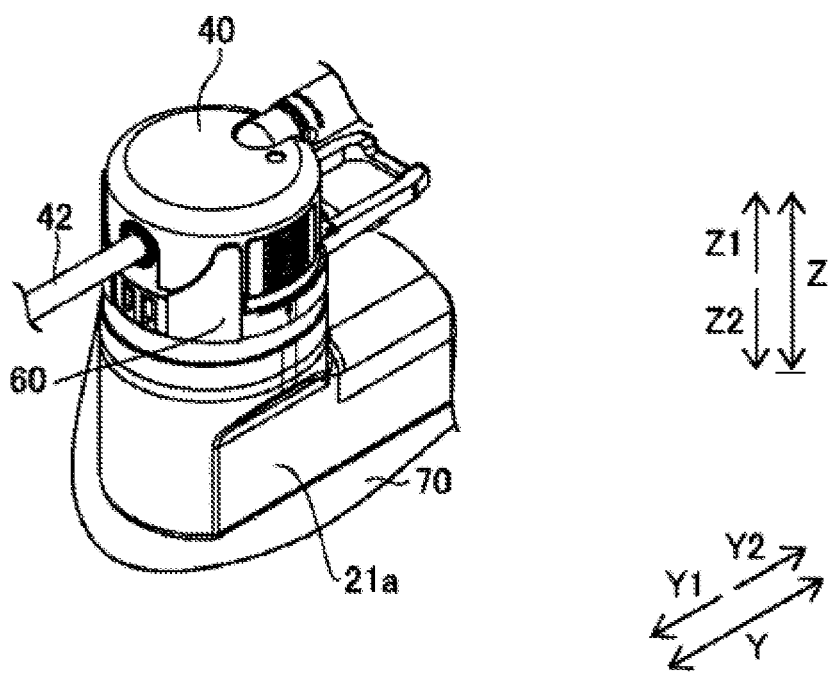
FIG. 20 is a diagram illustrating a perspective view of a state of a second embodiment where the surgical instrument is attached to the robot arm through the adaptor.

As illustrated in FIG. 17, the adaptor 60 is attached to the robot arm 21a with the robot arm 21a covered by the drape 70. The adaptor 60 is moved in the Z direction with respect to the robot arm 21a to be attached to the robot arm 21a. As illustrated in FIGS. 18 and 19, the surgical instrument 40 is attached to the adaptor 60 attached to the robot arm 21a. The surgical instrument 40 is moved in the Y direction along the precedence guide sections 69, the precedence guide rail 64, the first guide rail 63a, and the second guide rail 63b of the adaptor 60 and thereby attached to the adaptor 60. In this way, the surgical instrument 40 is attached to the robot arm 21a through the adaptor 60 as illustrated in FIG. 20.

When detaching the surgical instrument 40 from the robot arm 21a, the surgical instrument 40 is slid and moved in the Y2 direction while pressing the button 461 of the movable member 46 of the surgical instrument 40 and then detached from the adaptor 60.

(Attachment of Surgical Instrument to Adaptor)

With reference to FIGS. 21 to 26, attachment of the surgical instrument 40 to the adaptor 60 by the guiding by the precedence guide sections 69 is described.

As illustrated in FIGS. 21 and 24, the surgical instrument 40 is located in the Z1 side of the adaptor 60 such that the protrusions 49 of the surgical instrument 40 come into contact with the precedence guide sections 69 of the adaptor 60.

As illustrated in FIGS. 22 and 25, the surgical instrument 40 is moved in the Y1 direction while guiding the protrusions 49 by the precedence guide sections 69. In this process, the surgical instrument 40 is guided by the precedence guide rail 64 first, and then the surgical instrument 40 is guided by the first guide rail 63a and the second guide rail 63b.

As illustrated in FIGS. 23 and 26, once the surgical instrument 40 is mounted to the adaptor 60, the protrusions 49 of the surgical instrument 40 are engaged with the attachment engagement sections 611 of the adaptor 60.

Other configurations of a second embodiment are similar to those of an above-described first embodiment.

(Modifications)

It should be understood that the embodiments disclosed herein are illustrated by way of example in every respect and do not limit the invention. The scope of the present invention is indicated by claims, not by explanation of the embodiments, and includes equivalents to claims and all alterations (modifications) within the same.

For example, the surgical instrument is attached or detached by being slid and moved in the shaft-extending direction along the second surface of the adaptor in the examples illustrated in above-described first and second embodiments, but the invention is not limited thereto. In an embodiment or a modification, the surgical instrument may be attached or detached by being slid and moved in a direction crossing the shaft-extending direction along the second surface of the adaptor.

The adaptor is in a substantial circle shape in plan view in the example illustrated in an above-described first embodiment, but the invention is not limited thereto. In an embodiment or a modification, the shape of the adaptor in plan view may not be the substantial circle. For example, the adaptor may be in a rectangular shape in plan view.

The four drive transmission members are provided on the adaptor in the examples illustrated in above-described first and second embodiments, but the invention is not limited thereto. For example, in an embodiment or a modification, the number of the drive transmission members provided on the adaptor may be other than four.

The adaptor and the drape are provided separately in the examples illustrated in above-described first and second embodiments, but the invention is not limited thereto. For example, in an embodiment or a modification, the adaptor and drape may be provided integrally.

The invention claimed is:

1. An adaptor for detachably connecting a surgical instrument to a robot arm of a robotic surgical system, comprising:
   a base body including a first surface to be attached to the robot arm and a second surface to which an attachment surface of the surgical instrument is mounted; and
   drive transmission members rotatably provided on the base body, wherein
   the second surface of the base body includes a first guide rail and a second guide rail respectively corresponding to a first guide groove and a second guide groove provided on the attachment surface of the surgical instrument,
   the first and second guide rails of the second surface are configured to be inserted respectively into the first and second guide grooves of the attachment surface, and guide the surgical instrument to be slid to a position where the drive transmission members respectively correspond to rotation members provided on the attachment surface of the surgical instrument,
   the drive transmission members respectively include engagement sections configured to be engaged with the corresponding rotation members provided on the attachment surface,
   the engagement sections include:
      a first engagement section which is provided in a first drive transmission member of the drive transmission members that is located on an upstream side in a slide insertion direction; and
      a second engagement section which is provided in a second drive transmission member of the drive transmission members that is located on a downstream side in the slide insertion direction, wherein the second engagement section is formed in a different shape from the first engagement section.

2. The adaptor according to claim 1, wherein
   each of the drive transmission members includes a first member and a second member provided movably with respect to the first member with a bias member interposed in between, and
   the first and second guide rails of the second surface guide the first and second guide grooves of the surgical instrument in a direction crossing a direction in which the second member moves with respect to the first member.

3. The adaptor according to claim 1, wherein
   the second surface of the base body includes a precedence guide rail that is provided between the first and second guide rails correspondingly to a precedence guide groove provided on the attachment surface of the surgical instrument and configured to guide the surgical instrument before the first and second guide rails guide the surgical instrument.

4. The adaptor according to claim 3, wherein
   an upstream side of the precedence guide rail in the slide insertion direction thereof is formed in a tapered shape.

5. The adaptor according to claim 1, wherein
   the first and second guide rails each include a tab section to be engaged with an engagement hole provided in the corresponding one of the first and second guide grooves.

6. The adaptor according to claim 5, wherein
   the first and second guide rails each include a rail section that is slidably inserted into the corresponding one of the first and second guide grooves and a jut section that is provided to the rail section on an opposite side of the tab section and is to be engaged with an engagement groove formed in the corresponding one of the first and second guide grooves.

7. The adaptor according to claim 1, wherein the second surface of the base body includes a first electrode array and a groove configured to receive a protrusion provided in a second electrode array which is provided on the attachment surface of the surgical instrument and is to be connected to the first electrode array.

8. The adaptor according to claim 1, wherein the first engagement section is formed in a shape that avoids engagement with the rotation member that is engaged with the second engagement section.

9. The adaptor according to claim 1, wherein the first drive transmission member includes, on a side of the second surface, the first engagement section including a first recess and a second recess that are separately formed, and
the second drive transmission member includes, on a side of the second surface, the second engagement section formed as one recess in a shape in which the first recess and the second recess are connected with each other.

10. The adaptor according to claim 1, wherein the slide insertion direction is substantially parallel to a direction in which a shaft of the surgical instrument extends.

11. The adaptor according to claim 1, wherein the adaptor is a drape adaptor that is to be attached to the robot arm with a drape between the adaptor and the robot arm.

12. The adaptor according to claim 1, further comprising:
a precedence guide section that protrudes from the base body along a direction parallel to a direction in which the first and second guide rails extend and that is configured to guide the surgical instrument before the first and second guide rails guide the surgical instrument.

13. The adaptor according to claim 12, wherein the precedence guide section guides a protrusion, which protrudes from the attachment surface of the surgical instrument toward the second surface, in the direction in which the first and second guide rails extend.

14. The adaptor according to claim 13, wherein the second surface of the base body includes an attachment engagement section with which the protrusion of the attachment surface of the surgical instrument is engaged.

15. The adaptor according to claim 12, wherein the precedence guide section comprises a pair of precedence guide sections provided substantially in parallel to the first surface and the second surface and substantially in parallel to each other at a predetermined interval in a direction orthogonal to a direction in which the surgical instrument is guided.

16. The adaptor according to claim 15, further comprising:
a connection section that connects end sections of the pair of precedence guide sections on the upstream side in the slide insertion direction.

17. The adaptor according to claim 12, further comprising:
a contact section that is provided in an end section of the base body on the downstream side in the slide insertion direction to protrude toward the surgical instrument, such that the surgical instrument comes into contact with the contact section when the surgical instrument is attached to the adaptor.

18. An adaptor for detachably connecting a surgical instrument to a robot arm of a robotic surgical system, comprising:
a base body including a first surface to be attached to the robot arm and a second surface to which an attachment surface of the surgical instrument is mounted; and
a drive transmission member rotatably provided on the base body, wherein
the second surface of the base body includes a first guide rail and a second guide rail respectively corresponding to a first guide groove and a second guide groove provided on the attachment surface of the surgical instrument, and
the first and second guide rails of the second surface are configured to be inserted respectively into the first and second guide grooves of the attachment surface, to guide the surgical instrument to be slid to a position where the drive transmission member corresponds to a rotation member provided on the attachment surface of the surgical instrument, wherein
the adaptor further comprises a precedence guide section that protrudes from the base body along a direction parallel to a direction in which the first and second guide rails extend and that is configured to guide the surgical instrument before the first and second guide rails guide the surgical instrument.

19. A method of attaching a surgical instrument to a robot arm of a robotic surgical system through an adaptor, comprising:
attaching a first surface of a base body of the adaptor to the robot arm;
bringing a protrusion protruding from an attachment surface of the surgical instrument into contact with a precedence guide section formed to protrude from the base body;
moving the surgical instrument in a slide insertion direction while the protrusion is slidably guided by the precedence guide section;
inserting a first guide rail and a second guide rail provided on a second surface of the base body respectively into a first guide groove and a second guide groove provided on the attachment surface, and moving the surgical instrument with respect to the adaptor to a position where drive transmission members rotatably provided on the base body respectively correspond to rotation members provided on the attachment surface while the first and second guide rails are slidably guided by the first and second guide grooves, wherein the precedence guide section extends along a direction parallel to a direction in which the first and second guide rails extend; and
engaging the protrusion of the surgical instrument with an attachment engagement section of the adaptor.

* * * * *